US00PP09706P

United States Patent [19]

Ilsink

[11] Patent Number: Plant 9,706

[45] Date of Patent: Nov. 26, 1996

[54] HYBRID TEA ROSE PLANT NAMED 'INTERZENA'

[75] Inventor: G. P. Ilsink, Doorn, Netherlands

[73] Assignee: DeVor Nurseries, Inc., Watsonville, Calif.

[21] Appl. No.: 596,709

[22] Filed: Feb. 5, 1996

[51] Int. Cl.[6] ..... A01H 5/00

[52] U.S. Cl. ..... Plt./11

[58] Field of Search ..... Plt./11, 12, 18, Plt./19, 20

*Primary Examiner*—Howard J. Locker

*Attorney, Agent, or Firm*—Christie, Parker & Hale, LLP

[57] ABSTRACT

A new variety of hybrid tea rose plant producing pink blend flowers.

1 Drawing Sheet

SUMMARY OF THE INVENTION

The present invention relates to a new and distinct variety of rose of the hybrid tea rose class which was originated by my crossing as seed parents two unnamed, unpatented, undistributed, proprietary seedlings of my creation. The varietal denomination of this new rose is 'Interzena'.

Among the novel characteristics possessed by this new variety which distinguishes it from its parents are its ability to produce commercially desirable cut flowers for the cut flower market. Plants of the new variety have attractive foliage and produce flowers of good bud and flower form.

Asexual reproduction by budding and grafting of the new variety as performed in Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and environmental conditions.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class: Hybrid tea

The following information is from observations made of specimens grown under glass in Watsonville, Calif. in the month of November.

FLOWER

Blooming habit: Continuous.

A. Bud:

(1) *Size.*—Medium, about 5 to 6 cm.

(2) *Form.*—Pointed.

(3) *Color.*—As sepals divide, bud color is near 63A.

(4) *Sepals.*—About 4 to 5 sepals are lanceolate and 1 sepal may be lanceolate with a leaf shaped top; length about 4 to 6 cm; near 147B.

(5) *Peduncle.*—Length: About 7 to 10 cm. Aspect: Smooth with small prickles. Strength: Sturdy, erect. Color: Near 141C.

(6) *Bracts.*—1 to 2 per bud. Color — near 136B. Form — lanceolate with caudate apex. Location in relation to flower — about 6 to 9 cm below calyx.

B. Bloom:

(1) *Size.*—About 11 to 12 cm.

(2) *Borne.*—Singly.

(3) *Form.*—High centered at first, becoming imbricated at maturity.

(4) *Petalage.*—Number of petals under normal conditions — about 20 to 24.

(5) *Color* (⅓ *to* ½ open).13 Outer petals — Top surface — top part of petal is near 63B, middle part of petal is near 68C and bottom part of petal is near 62D. Under surface — top part of petal is near 63A, middle part of petal is near 68B and bottom of petal is near 65D. Inner petals — Top surface — top part of petal is near 63A; middle part of petal is near 68B and bottom part of petal is near 65D. Undersurface — same as top surface of inner petal. Base of petals — near 157A. General tonality from a distance — two-toned pink.

(6) *Color (fully open).*—Outer petals — Top surface outer edge — near 63C fading for the rest of the petal to near 65D. Undersurface — Outer edge of petal is near 65A with rest of petal being faded to near 65C. Inner petals — Top surface near 63B fading down to near 63C. — Undersurface top of petal near 63B fading for rest of petal to Near 63C. Base of petals — Near 157B. General tonality from a distance — pink.

(7) *Color change.*—Goes from a two-toned pink bud to open to a consistent looking pink open bloom. Petal top surface — Edging lightens to form a more even color. Petal undersurface — Edging lightens to form a more even color. Base of petal lightens. General tonality from a distance — pink.

C. Petals:

(1) *Texture.*—Thick.

(2) *Appearance.*—Inside velvety; outside satiny.

(3) *Form.*—Elliptic, reflexes upon maturity.

(4) *Arrangement.*—Imbricated.

(5) *Petaloids in center.*—None.

(6) *Persistence.*—Petals drop off cleanly.

(7) *Fragrance.*—None detected.
(8) *Lasting quality.*—On plant about 10 to 12 days; about 8 to 10 days in vase after cutting.

REPRODUCTIVE ORGANS

A. Stamens, filaments and anthers:
*Arrangement.*—Introrse.
*Filaments.*—Color near 15D.
*Anthers.*—Color near 20A.
*Pollen.*—Color near 20A.
B. Styles: color near 2D.
*Stigma.*—Color near 10C.

PLANT

A. Form: Upright.
B. Growth: Very vigorous about 145 to 200 cm in greenhouse under glass.
C. Foliage:
(1) *Size.*—Large.
(2) *Quantity.*—Abundant.
(3) *Color.*—New foliage: Upper side near 131A. Underside near 133A. Old foliage: Upper side near 131A. Underside near 133A.
(4) *Shape.*—Ovate.
(5) *Texture.*—Upper side is shiny and underside is dull.
(6) *Edge.*—Serrated.
(7) *Serration.*—Serrate.
(8) *Petiole color.*—Top surface — near 137A. Underside near 137B.
(9) *Stipules.*—Adnate.
(10) *Auricle.*—Narrow triangular auricle facing forward.
(11) *Rachis.*—Smooth.
(12) *Resistance to disease.*—Very resistant to mildew, rust and blackspot.
D. Wood:
(1) *New wood.*—Color — near 178A. Bark — smooth.
(2) *Old wood.*—Bark — smooth.
(3) *Flower stem length from last cutting.*—About 45 to 60 cm.
E. Thorns:
(1) *Thorns.*—Quantity — few on basal canes and laterals; about 4 to 5 cm, curved and slightly hooked; position irregular; color near 181C.
(2) *Prickles.*—Some.
F. Winter hardiness: Completely winter hardy in Watsonville, Calif.

I claim:

1. A new and distinct variety of rose plant of the hybrid tea rose class, substantially as shown and described.

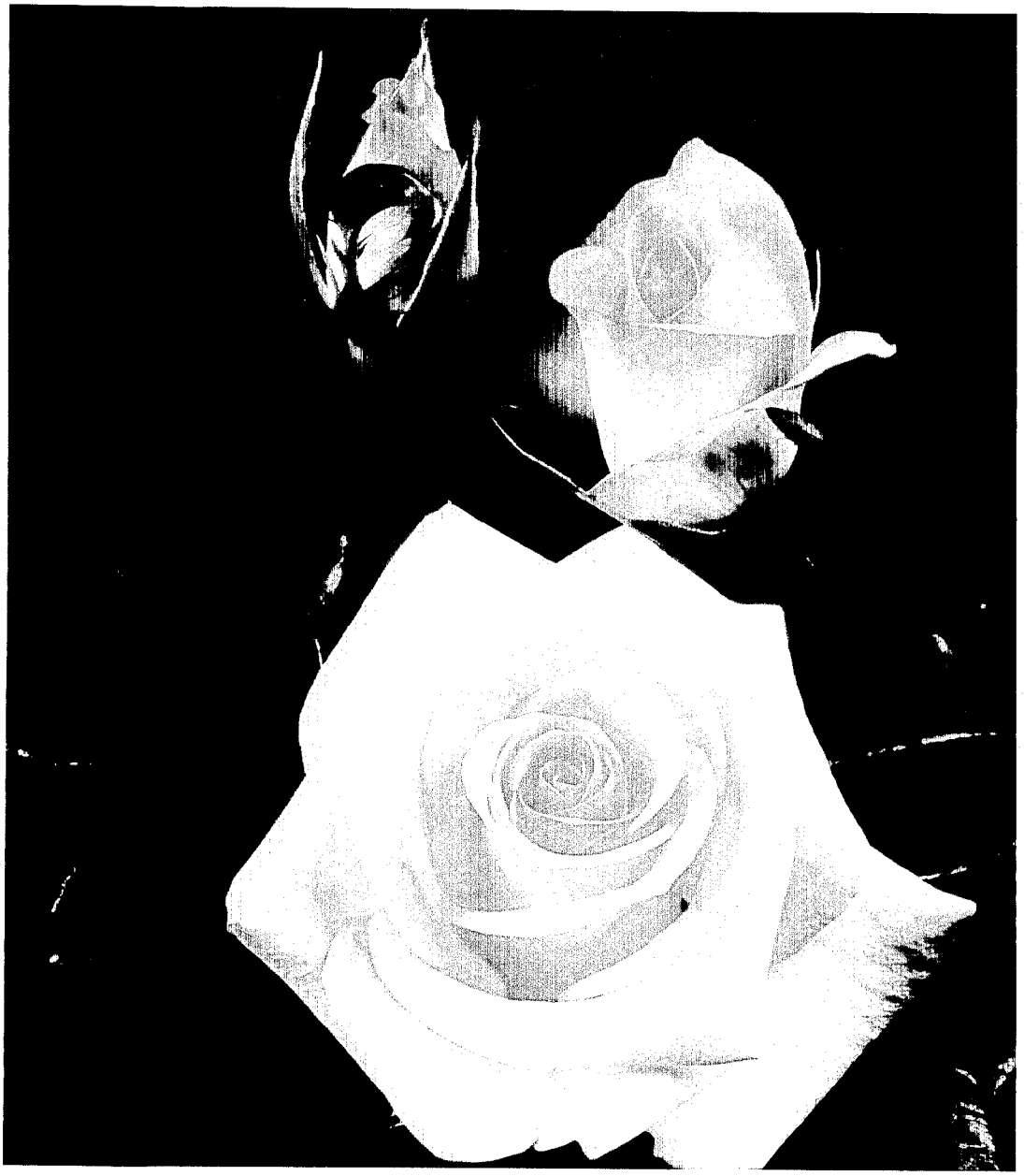

* * * * *